(12) United States Patent
Rabaeh et al.

(10) Patent No.: US 12,138,475 B2
(45) Date of Patent: Nov. 12, 2024

(54) COMPOSITION OF POLYMER GEL DOSIMETERS FOR RADIATION THERAPY

(71) Applicant: The Hashemite University, Zarqa (JO)

(72) Inventors: Khalid A. Rabaeh, Zarqa (JO); Feras M. Aldweri, Zarqa (JO); Nesreen I Udwan, Zarqa (JO); Manar K Sowan, Zarqa (JO); Ala'a A Abu Sa'aleek, Zarqa (JO)

(73) Assignee: Hashemite University, Zarqa (JO)

( * ) Notice: Subject to any disclaimer, the term of this patent is extended or adjusted under 35 U.S.C. 154(b) by 673 days.

(21) Appl. No.: 17/388,506

(22) Filed: Jul. 29, 2021

(65) Prior Publication Data

US 2023/0047643 A1 Feb. 16, 2023

(51) Int. Cl.

| | |
|---|---|
| *A61N 5/10* | (2006.01) |
| *C08F 2/10* | (2006.01) |
| *C08F 2/46* | (2006.01) |
| *C08F 20/56* | (2006.01) |
| *C08F 26/06* | (2006.01) |
| *C08K 5/053* | (2006.01) |
| *C08K 5/50* | (2006.01) |
| *C08K 11/00* | (2006.01) |

(52) U.S. Cl.
CPC ............. *A61N 5/1029* (2013.01); *C08F 2/10* (2013.01); *C08F 2/46* (2013.01); *C08F 20/56* (2013.01); *C08F 26/06* (2013.01); *C08K 5/053* (2013.01); *C08K 5/50* (2013.01); *C08K 11/00* (2013.01)

(58) Field of Classification Search
CPC ....... C08F 2/10; C08F 220/54; C08F 222/385
See application file for complete search history.

(56) References Cited

U.S. PATENT DOCUMENTS

| | | | | |
|---|---|---|---|---|
| 2014/0332693 | A1* | 11/2014 | Basfar | A61K 49/06 424/9.3 |
| 2019/0146097 | A1* | 5/2019 | Maeyama | C08L 33/02 436/58 |

FOREIGN PATENT DOCUMENTS

BR  102020013494 A2 *  1/2022

OTHER PUBLICATIONS

Rabaeh et al. Journal of Radioanalytical and Nuclear Chemistry 331: 3147-3153 (Year: 2022).*
Senden et al. Journal of Physics: Conference Series 56, 156 (Year: 2006).*

(Continued)

*Primary Examiner* — Mark S Kaucher
(74) *Attorney, Agent, or Firm* — Geeta Kadambi; RIDDHI IP LLC

(57) ABSTRACT

New compositions of tissue-equivalent three-dimensional polymer gel dosimeters based on acrylamide (AAm), N-isopropylacrylamide (NIPAM), N-(Hydroxymethyl)acrylamide (NHMA), diacetone acrylamide (DAAM) and N-Vinylcaprolactam (NVCL) monomer with ethylene glycol co-solvent have been introduced in this invention for radiotherapy dosimetry. The dosimeter was irradiated with 6 and 15 MV linear accelerator at absorbed doses up to 10 Gy. The nuclear magnetic resonance (NMR) spin-spin relaxation rate ($R_2$) for water proton surrounding polymer formation was used to investigate the degree of polymerization of the five gels. The effect of additives, dose rate, radiation energy, stability of the polymerization after irradiation, were investigated on the dose response of the gels.

13 Claims, 3 Drawing Sheets

(56) References Cited

OTHER PUBLICATIONS

Adenan Journal of Physics: Conference Series 1349, Jan. 21, 2019 (Year: 2019).*

Jirasek et al. Physics in Medicine & Biology 51, 1891-1906 (Year: 2006).*

M Yoshioka et.al., A new polymer gel dosimeter composed of methacrylic acid, agarose gel and THPC with gelatin, Journal of Physics: Conference Series 164 (2009) Jan. 2013.

A J Venning et.al., Investigation of the PAGAT polymer gel dosimeter using magnetic resonance imaging, Phys. Med. Biol. 50 (2005) 3875-3888.

Mahbod Sedaghat et al., Severe dose inaccuracies caused by an oxygen-antioxidant imbalance in normoxic polymer gel dosimeters, Phys. Med. Biol. 56 (2011) 601-625.

Khalid A. Rabaeh et al., High dose sensitivity of N-(isobutoxymethyl)acrylamide polymer gel dosimeters with improved monomer solubility using acetone co-solvent, Nuclear Inst. and Methods in Physics Research B 442 (2019) 67-72.

Khalid A. Rabaeh et al., New normoxic N-(Hydroxymethyl)acrylamide based polymer gel for 3D dosimetry in radiation therapy, Physica Medica 33 (2017) 121-126.

Belal Moftah et al., Novel 3D polymer gel dosimeters based on N-(3-Methoxypropyl)acrylamide (NMPAGAT) for quality assurance in radiation oncology, Radiation Measurements 135 (2020) 106372.

Marek J. Maryanski et al., NMR Relaxation Enhancement in Gels Polymerized and Cross-Linked by Ionizing Radiation: a New Approach to 3D Dosimetry by MRI, Magnetic Resonance Imaging, vol. II. pp. 253-258, 1993.

Peter M Fong et al., Polymer gels for magnetic resonance imaging of radiation dose distributions at normal room atmosphere, Phys. Med. Biol. 46 (2001) 3105-3113.

Y. De Deene et al., Validation of MR-Based Polymer Gel Dosimetry as a Preclinical Three-Dimensional Verification Tool in Conformal Radiotherapy, Magnetic Resonance in Medicine 43:116-125 (2000).

A Jirasek et al. Effects of glycerol co-solvent on the rate and form of polymer gel dose response, Phys. Med. Biol. 54 (2009) 907-918.

C. Hurley et al., A study of a normoxic polymer gel dosimeter comprising methacrylic acid,gelatin and tetrakis (hydroxymethyl) phosphonium chloride (MAGAT), Applied Radiation and Isotopes 63 (2005) 443-456.

Shin-ichiro Hayashi et al., Effect ofinorganicsaltonthedosesensitivityofpolymergeldosimeter, Radiation PhysicsandChemistry81(2012)884-888.

Samer I. Awad et al., 3-D Quality Assurance in CyberKnife Radiotherapy Using a Novel N-(3-methoxypropyl) Acrylamide Polymer Gel Dosimeter and Optical CT, Radiation Physics and Chemistry 161 (2019) 34-41.

\* cited by examiner

COMPOSITION OF POLYMER GEL DOSIMETERS FOR RADIATION THERAPY

FIELD OF INVENTION

In the instant application tissue equivalent polymer gels that form three dimensional gels for dosimeter and are effectively used in radiotherapy treatment are disclosed.

BACKGROUND

Medical radiation dosimetry is essential to improve patient survival rates. As a therapeutic method, it may be the primary technique in conjunction with surgery and chemotherapy provided by medical oncologists. Therefore, the dosimeter must have a high accuracy and ideally be tissue equivalent. It should be independent of direction and insensitive to photon energy and dose rate (Rabaeh K. A. et.al. 2019). There are several dosimeters currently used to determine radiation dose in radiotherapy treatment planning. These include ionization chambers, radiographic film, diode detectors, thermo luminescent detectors (TLD). Unfortunately, these dosimeters are used for only one or two-dimensional dosimeters and so are limited in their ability to integrate dose over a three-dimensional volume (Lepage et.al. 2001). There is a need for three-dimensional dosimeter gel that mimic body tissue.

SUMMARY

The present invention relates to polymer gel dosimeter for radiotherapy treatment planning system. In one embodiment a dosimeter is made using five types of three-dimensional gels are described. In another embodiment, a method of making a radiation-induced polymerization of acrylamide (PAGAT), N-isopropylacrylamide (NIPAMGAT), N-(Hydroxymethyl)acrylamide (NHMAGAT) diacetone acrylamide polymer (DAAMGAT) and N-Vinylcaprolactam (NVCL) gels are disclosed. The nuclear magnetic resonance (NMR) spin-spin relaxation rate ($R_2$) for water proton surrounding polymer formation was used to investigate the degree of polymerization of gel dosimeters.

In another embodiment, five different compositions of polymer gel dosimeters are introduced in this invention based on radiation induced polymerization of AAm, NIPAM, NHMA, DAA and NVCL for radiotherapy treatment planning. The degree of polymerization of these gels were characterized by the nuclear magnetic resonance (NMR) spin-spin relaxation rate ($R_2$) for water proton surrounding polymer formation, The change in relaxation rate ($\Delta R_2$) corresponding to the amount of polymer formation in the four types of gels (i.e. PAGAT, NIPAMGAT, NHMAGAT, NVCL and DAAGAT) increases gradually with absorbed dose up to 10 Gy.

In another embodiment, the dose sensitivity for the five types of gels increases gradually with increase of ethylene glycol concentration from 0 to 20% within gel dosimeters. In another embodiment, no remarkable effect of dose rate and radiation energy on the performance of irradiated the four types of gels were found. In another embodiment, the stability of unirradiated and irradiated these polymer gel dosimeters was studied, and it was found there is no remarkable change in the $\Delta R_2$ of the unirradiated and irradiated gel dosimeters up to one week.

BRIEF DESCRIPTION OF DRAWINGS

Example embodiments are illustrated by way of example and not limitation in the figures of the accompanying drawings, in which like references indicate similar elements and in which.

Figure 1:
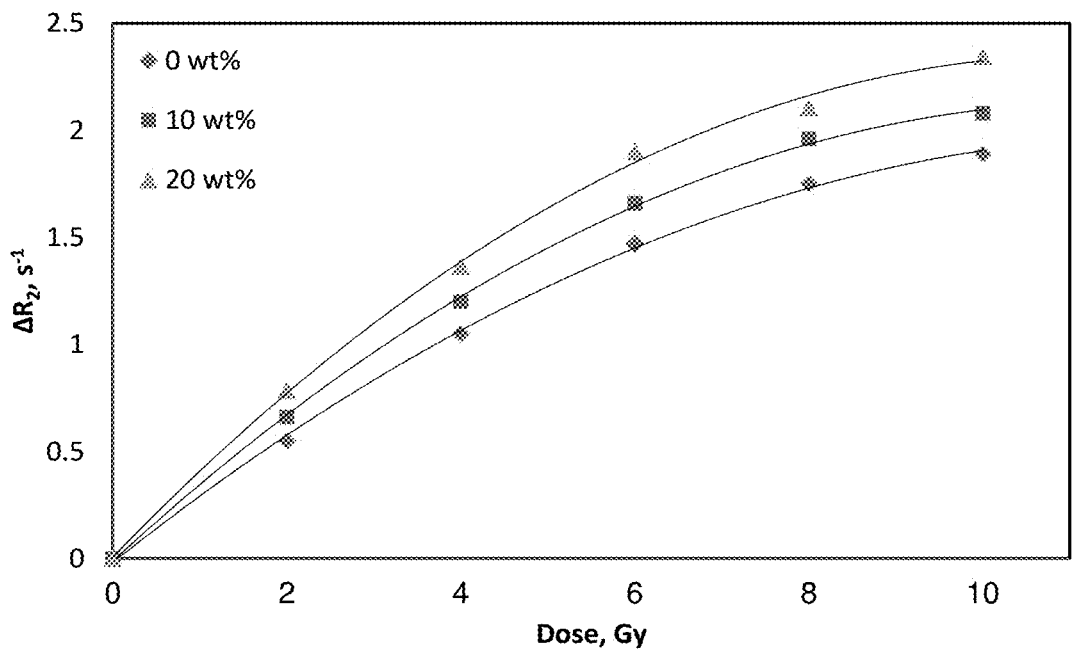
FIG. 1: Change in relaxation rate ($\Delta R2$) of PAGAT (1, 2 and 3) polymer gel with the different concentration of ethylene glycol.

Others features of the present embodiments will be apparent from the accompanying drawings and from the detailed description that follows.

DETAILED DESCRIPTION

In the instant disclosure various formulations of polymer gel dosimeters for the measurement of three-dimensional (3D) dose distributions of ionizing radiation are disclosed. The polymer gel is a tissue equivalent material and upon irradiation it polymerizes in an aqueous gelatin matrix. It was found that polymer gel dosimeters, alongside with Magnetic resonance Imaging (MRI) can be used to image the spatial 3D dose distribution for radiotherapy treatment planning (De Deene et.al. 2000).

Fong, P. M., et.al. (2001), proposed the first type of normoxic gel, which known as MAGIC. The dosimeter was composed of methacrylic, gelatin, hydroquinone, ascorbic acid, copper (II) sulphate, and ascorbic acid. This dosimeter could be prepared in a normal environment without purging nitrogen. Another polymer gel prepared in this way is ABAGIC (acrylamide, N,N'-methylene-bis-acrylamide (BIS), gelatin, initiated by copper (II) sulphate, ascorbic acid and hydroquinone). These dosimeters were based upon the polymerization of methacrylic acid (MAA) infused with copper (II) sulphate and the antioxidant ascorbic acid in a gel matrix.

Yenning, A. et. al. (2005), investigated PAGAT polymer gel dosimeter using MRI scanning PAGAT polymer gel dosimeter has been combined with the antioxidant tetrakis (hydroxymethyl) phosphonium chloride (THPC) and the polymerization inhibitor hydroquinone (HQ) to form the normoxic PAGAT polymer gel dosimeter. The $R_2$-dose response of the PAGAT polymer gel dosimeters determined in this study was found to have a linear range up to 7 Gy with $R_2$-dose sensitivity of $(0.183 \pm 0.005)$ s$^{-1}$ Gy$^{-1}$.

Another group (Hurley et.al. 2005) studied the dose response of the normoxic polymer gel dosimeter comprising THPC with methacrylic acid (MAA) and gelatin, which called MAGAT. The temporal stability of the MAGAT polymer gel dosimeter was found to be stable over a period of 1 week with the background, $R_2$ steadily increasing and the slope of the $R_2$-dose response decreasing over this time period. The spatial stability of the MAGAT polymer gel dosimeter was found to have a penumbra of around 3.5 mm, 1 day post-irradiation that is consistent with results from other gel dosimeter formulations.

A new type of methacrylic acid-based gel dosimeter was made with agarose and gelatin with different roles, respectively (Yoshioka et.al. 2009). The gel samples were irradiated to 6 MV photon beam of a medical linear accelerator, the samples were irradiated up to 15 Gy for the study of dose-$R_2$ response relations, all images were acquired with 0.3 T open MRI system using a multiple spin-echo sequence, all dose-R2 response curves were acquired after one day post-irradiation. The long-term stability of $R_2$ was examined in the period of 3-240 hours post-irradiation. The dose-$R_2$ response was comparable with that of the conventional MAA gel system. This gel appears to be a promising dosimeter because it minimizes both the structure relaxation of gelatin at storing and the melting of the gel by the exothermic polymerization reaction.

Previously gels were composed of N-isopropyl-acrylamide (NIPAM), N,N'-methylene-bis-acrylamide (BIS), gelatin, glycerol) and de-ionized water. (THPC) was used as an oxygen scavenger. Relative fractions of monomer and cross-linker were kept at 50%, while the relative amount of total monomer+crosslinker in the gel was varied (Jirasek et. al. 2009). A remarkable increase in dose sensitivity of polymer gels was found by increasing glycerol concentrations within polymer gel.

In another study it was observed that the severe dose inaccuracies caused by an oxygen-antioxidant imbalance in normoxic polymer gel dosimeters (Sedaghat et. al. (2011). Two oxygen scavengers have been successfully tested to produce normoxic polymer gel dosimeters under normal atmospheric conditions. The first is ascorbic acid and the second is a chloride (also sulfate) salt of tetrakis (hydroxymethyl) phosphonium. These antioxidants, added to the dosimeter during gel preparation, it was observed that oxygen and excess antioxidant are an important cause of inaccuracy in normoxic polymer gel dosimeters.

Another group evaluated the effect of inorganic salts on the dose sensitivity of methacrylic-acid-based polymer gel dosimeter (Hayashi et. al (2012). Methacrylic-acid-based gels were prepared using distilled water, gelatin (300 bloom), methacrylic acid and tetrakis-hydroxymethyl-phosphonium chloride (THPC, 80%) as an oxygen scavenger. Each dosimeter contains the same amounts of water, MA, gelatin and THPC, but different amounts of additives (i.e., lithium chloride, sodium chloride, potassium chloride or magnesium chloride hexahydrate, where the water of hydration of magnesium chloride joined the water molecules already in the solution). The results demonstrated that the dose response of methacrylic-acid-based polymer gel dosimeters is increased by the addition of inorganic salts.

A novel composition of N-(Hydroxymethyl)acrylamide (NHMA) for radiation therapy was used as dosimeters and were irradiated by 6, 10 and 18 MV photon beams of a medical linear accelerator at various dose rates to doses of up to 20 Gy (Rabaeh et.al. 2017). The dose response of polymer gel dosimeters was studied using NMR in terms of relaxation rate of hydrogen protons within the water molecule. Also, the gel response was studied using absorption spectroscopy and found that this novel gel can be successfully utilized 3D dosimetry. They found no appreciable effects of dose rate and beam energy on the gel dosimeter performance in both relaxation rate and absorbance measurements.

Moftah et.al.(2020), introduced an anoxic and normoxic N-(3-methoxypropyl) acrylamide (NMPA) polymer gel dosimeters for radiotherapy dosimetry. The dosimeters contain different concentration of NMPA and BIS with 5 wt % gelatine and 10 mM THPC as an antioxidant agent. The gels were irradiated to various absorbed doses up to 20 Gy with 10 MV beam energy and 200 cGy/min dose rate. They reported a significant increase in dose response in terms of $R_2$ with increasing co-monomer concentration. A reasonable increase in the performance of this dosimeter was noticed after adding glycerin to the gel.

In the present disclosure different polymer compositions and method of making them is described. Different compositions of normoxic PAGAT, NIMPAGAT, NHMAGAT, DAAMGAT and NVCLGAT polymer gel dosimeters, with different concentrations of ethylene glycol were prepared in this invention for radiotherapy dosimetry as listed in table 1, 2, 3, 4 and 5. Chemicals were obtained from SIGMA Chemical Co (St. Louis, Mo., USA). All gel were fabricated under a fume hood in normal atmospheric condition. Gelatin powder was added to the ultra-pure de-ionized water and left for 10 minutes to soak at room temperature before heated up to 50° C., and magnetically stirred for 30 minutes to make sure that the gelatin is totally dissolved. After the solution was cooled down to 45° C., BIS, monomer (i.e. AAm (Table 1) or NIPAM (Table 2) or NHMA (Table3) or DAAM (Table 4) or NVCL (Table 5) and ethylene glycol were added respectively and kept stirring until completely dissolved. Next the solution was cooled down to 35° C., and THPC was added as antioxidant to remove all oxygen during the preparation process. The prepared gel solutions were filled into NMR tubes (1 cm diameter and 20 cm height, Wilmad glass, Buena, N.J., USA) and sealed. All gels were covered (to prevent photo-polymerization of the polymer gel) and stored in a refrigerator (10° C.).

A PAGAT polymer gel dosimeter composition comprising:

a) Acrylamide (AAm) monomer from 1 to 10%.
b) N, N'-methylene-bis-acrylamide (BIS) cross-linker from 1 to 4%.
c) Gelatin Type B from 1 to 10%.
d) Tetrakis (hydroxymethyl) phosphonium (THPC) from 5-20 mM.
e) Ethylene glycol from 0 to 50%.
f) De-ionized water as a solvent.

A NIPAMGAT polymer gel dosimeter composition comprising:

a) N-Isopropylacrylamide (NIPAM) monomer from 2 to 4%.
b) N, N'-methylene-bis-acrylamide (BIS) cross-linker from 1 to 4%.
c) Gelatin Type B from 1 to 10%.
d) Tetrakis (hydroxymethyl) phosphonium (THPC) from 1 to 20 mM.
e) Ethylene glycol from 0 to 50%.
f) De-ionized water as a solvent.

NHMAGAT polymer gel dosimeter composition comprising:

a) N-(Hydroxymethyl) acrylamide (NHMA) monomer from 2 to 10%.
b) N, N'-methylene-bis-acrylamide (BIS) cross-linker from 1 to 4%.
c) Gelatin Type B from 1 to 10%.
d) Tetrakis (hydroxymethyl) phosphonium (THPC) from 5 to 20 mM.
e) Ethylene glycol from 0 to 50%.
f) De-ionized water as a solvent.

DAAMGAT polymer gel dosimeter composition comprising:
a) Diacetone acrylamide (DAAM) monomer from 2 to 10%.
b) N, N'-methylene-bis-acrylamide (BIS) cross-linker from 1 to 4%.
c) Gelatin Type A from 1 to 10%.
d) Tetrakis (hydroxymethyl) phosphonium (THPC) from 5 to 20 mM.
e) Ethylene glycol from 0 to 50%.
f) De-ionized water as a solvent.

NVCLGAT polymer gel dosimeter composition comprising:
a) N-Vinylcaprolactam (NVCL) monomer from 2 to 10%.
b) N, N'-methylene-bis-acrylamide (BIS) cross-linker from 1 to 4%.
c) Gelatin Type A from 1 to 10%.
d) Tetrakis (hydroxymethyl) phosphonium (THPC) from 5 to 20 mM.
e) Ethylene glycol from 0 to 50%.
f) De-ionized water as a solvent.

The process of PAGAT polymer gel dosimeter preparation was as follows: The PAGAT polymer gels were fabricated under a fume hood in normal atmospheric conditions. The gelatin Type B was added to the ultra-pure de-ionized water and left for 10 minutes to soak before heated up to 50° C. for 1 hour. After the solution was cooled down to 45° C., BIS, AAm and ethylene glycol were added respectively and kept stirring until completely dissolved. After the solution cooled down to 35° C., THPC was added as antioxidant. For characterization study, the final polymer gels were filled into NMR tubes and sealed. All gels were stored in a refrigerator (10° C.) overnight prior to irradiation.

The process of NIPAMGAT polymer gel dosimeter preparation was as follows: The NIPAMGAT polymer gels were fabricated under a fume hood in normal atmospheric conditions. The gelatin Type B was added to the ultra-pure de-ionized water and left for 10 minutes to soak before heated up to 50° C. for 1 hour. After the solution was cooled down to 45° C., BIS, NIPAM and ethylene glycol were added respectively and kept stirring until completely dissolved. After the solution cooled down to 35° C., THPC was added as antioxidant. For characterization study, the final polymer gels were filled into NMR tubes and sealed. All gels were stored in a refrigerator (10° C.) overnight prior to irradiation.

The process of NHMAGAT polymer gel dosimeter preparation was as follows: The NHMAGAT polymer gels were fabricated under a fume hood in normal atmospheric conditions. The gelatin Type B was added to the ultra-pure de-ionized water and left for 10 minutes to soak before heated up to 50° C. for 1 hour. After the solution was cooled down to 45° C., BIS, NHMA and ethylene glycol were added respectively and kept stirring until completely dissolved. After the solution cooled down to 35° C., THPC was added as antioxidant. For characterization study, the final polymer gels were filled into NMR tubes and sealed. All gels were stored in a refrigerator (10° C.) overnight prior to irradiation.

The process of DAAMGAT polymer gel dosimeter preparation was as follows: The DAAMGAT polymer gels were fabricated under a fume hood in normal atmospheric conditions. The gelatin Type A was added to the ultra-pure de-ionized water and left for 10 minutes to soak before heated up to 50° C. for 1 hour. After the solution was cooled down to 45° C., BIS, DAAM and ethylene glycol were added respectively and kept stirring until completely dissolved. After the solution cooled down to 35° C., THPC was added as antioxidant. For characterization study, the final polymer gels were filled into NMR tubes and sealed. All gels were stored in a refrigerator (10° C.) overnight prior to irradiation.

The process of NVCLGAT polymer gel dosimeter preparation was as follows: The NVCLGAT polymer gels were fabricated under a fume hood in normal atmospheric conditions. The gelatin Type A was added to the ultra-pure de-ionized water and left for 10 minutes to soak before heated up to 50° C. for 1 hour. After the solution was cooled down to 45° C., BIS, NVCL and ethylene glycol were added respectively and kept stirring until completely dissolved. After the solution cooled down to 35° C., THPC was added as antioxidant. For characterization study, the final polymer gels were filled into NMR tubes and sealed. All gels were stored in a refrigerator (10° C.) overnight prior to irradiation.

TABLE 1

Compositions of PAGAT polymer gels with different concentrations of ethylene glycol (EG).

| Formulation code | Water (wt %) | Gelatin Type B (wt %) | AAm (wt %) | BIS (wt %) | EG (wt %) | THPC (mM) |
|---|---|---|---|---|---|---|
| PAGAT-1 | 89 | 5 | 3 | 3 | 0 | 10 |
| PAGAT-2 | 79 | 5 | 3 | 3 | 10 | 10 |
| PAGAT-3 | 69 | 5 | 3 | 3 | 20 | 10 |

TABLE 2

Compositions of NIPAMGAT polymer gels with different concentrations of ethylene glycol (EG).

| Formulation code | Water (wt %) | Gelatin Type B (wt %) | NIPAM (wt %) | BIS (wt %) | EG (wt %) | THPC (mM) |
|---|---|---|---|---|---|---|
| NIPAMGAT-1 | 89 | 5 | 3 | 3 | 0 | 10 |
| NIPAMGAT-2 | 79 | 5 | 3 | 3 | 10 | 10 |
| NIPAMGAT-3 | 69 | 5 | 3 | 3 | 20 | 10 |

TABLE 3

Compositions of NHMAGAT polymer gels with different concentrations of ethylene glycol (EG).

| Formulation code | Water (wt %) | Gelatin Type B (wt %) | NHMA (wt %) | BIS (wt %) | EG (wt %) | THPC (mM) |
|---|---|---|---|---|---|---|
| NHMAGAT -1 | 84 | 5 | 8 | 3 | 0 | 20 |
| NHMAGAT -2 | 74 | 5 | 8 | 3 | 10 | 20 |
| NHMAGAT -3 | 64 | 5 | 8 | 3 | 20 | 20 |

TABLE 4

Compositions of DAAMGAT polymer gels with different concentrations of ethylene glycol (EG).

| Formulation code | Water (wt %) | Gelatin Type A (wt %) | DAAM (wt %) | BIS (wt %) | EG (wt %) | THPC (mM) |
|---|---|---|---|---|---|---|
| DAAMGAT -1 | 89 | 5 | 3 | 3 | 0 | 10 |
| DAAMGAT -2 | 79 | 5 | 3 | 3 | 10 | 10 |
| DAAMGAT -3 | 69 | 5 | 3 | 3 | 20 | 10 |

TABLE 5

Compositions of NVCLGAT polymer gels with different concentrations of ethylene glycol (EG).

| Formulation code | Water (wt %) | Gelatin Type A (wt %) | NVCL (wt %) | BIS (wt %) | EG (wt %) | THPC (mM) |
|---|---|---|---|---|---|---|
| NVCLGAT -1 | 89 | 5 | 3 | 3 | 0 | 10 |
| NVCLGAT -2 | 79 | 5 | 3 | 3 | 10 | 10 |
| NVCLGAT -3 | 69 | 5 | 3 | 3 | 20 | 10 |

TABLE 6

Dose sensitivities of polymer gels without and with 20 wt % ethylene glycol (EG).

| Type of polymer gel | Dose sensitivity without EG (Gy$^{-1}$s$^{-1}$) | Dose sensitivity with 20 wt % EG (Gy$^{-1}$s$^{-1}$) | Dose range (Gy) |
|---|---|---|---|
| PAGAT | 0.24 | 0.31 | 0-6 |
| NIPAMGAT | 0.17 | 0.23 | 0-10 |
| NHMAGAT | 0.19 | 0.22 | 0-10 |
| DAAMGAT | 0.17 | 0.25 | 0-10 |
| NVCLGAT | 0.20 | 0.33 | 0-10 |

The irradiations were performed using 6 and 15 MV photon beam using medical linear accelerator with dose rate of 50 and 200 Gy/min. Each polymer gel samples were placed in a water phantom acrylic tank with dimensions 50×50 cm$^2$, the samples were immersed for approximately 3 cm under surface of water, the samples were irradiated with beam field size 10×10 cm$^2$ with different doses at 100 cm Source Surface Distance (SSD). After irradiation, all samples were transferred back to the refrigerator and kept for about 24 hours before the readout by NMR relaxometry.

The relaxation Rate ($R_2$) measurements were performed using 0.5 Tesla NMR relaxometry (Minispec, Bruker, Germany) A standard Malti-Spin-Echo Carr Purcell Meiboom Gill (CPMG) sequence was used to measure the relaxation time (T2) of unirradiated and irradiated gel samples in NMR tubes. Three samples set were measured for each absorbed dose point and the average value was presented in the figures of this invention. A standard sample was used to calibrate NMR instrument before measuring the gel dosimeters. The values of relaxation rate ($R_2=1/T_2$) can be obtained directly from the computer screen. The temperature during measurements was 20±0.1° C.

The effect of adding ethylene glycol on the dose response of the gel dosimeters was investigated by preparing different compositions of five types of polymer gel dosimeters containing different concentrations of ethylene glycol as listed in table 1, 2, 3, 4 and 5. Three dosimeters were irradiated for each selected absorbed, and the average response values in terms of $R_2$ were plotted as a function of absorbed dose (FIGS. 1, 2, 3, 4 and 5).

FIG. 1 shows change in relaxation rate (ΔR2) of PAGAT (1, 2 and 3) polymer gel with the different concentration of ethylene glycol.

Figure 2:
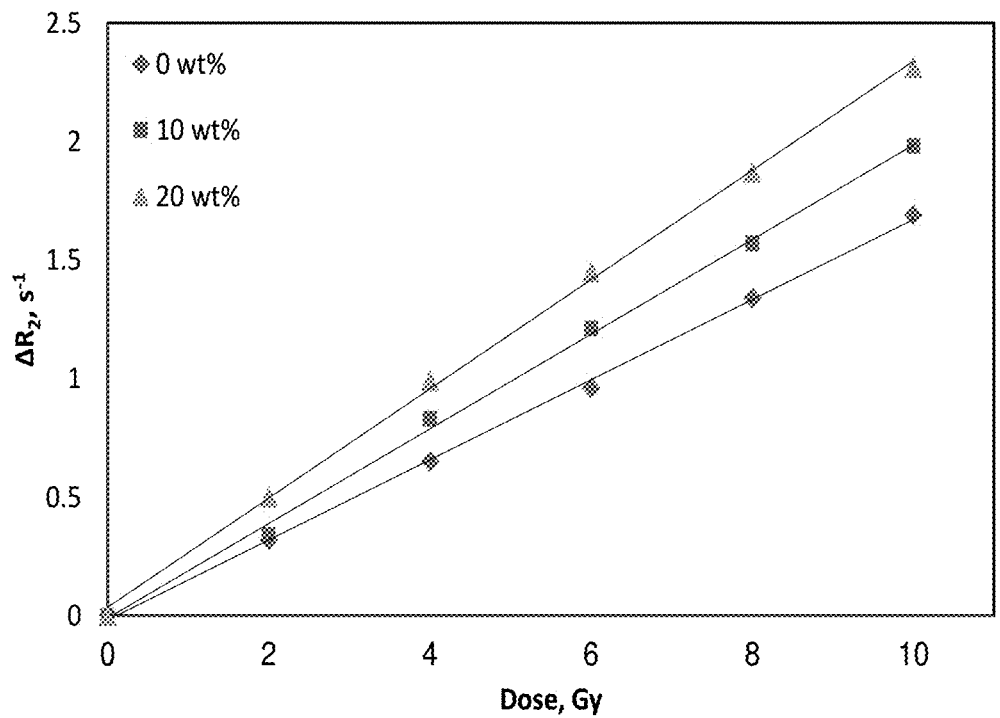
FIG. 2: Change in relaxation rate ($\Delta R2$) of NIMPAGAT (1, 2 and 3) polymer gel with the different concentration of ethylene glycol.

FIG. 2 shows change in relaxation rate (ΔR2) of NIMPAGAT (1, 2 and 3) polymer gel with the different concentration of ethylene glycol.

Figure 3:
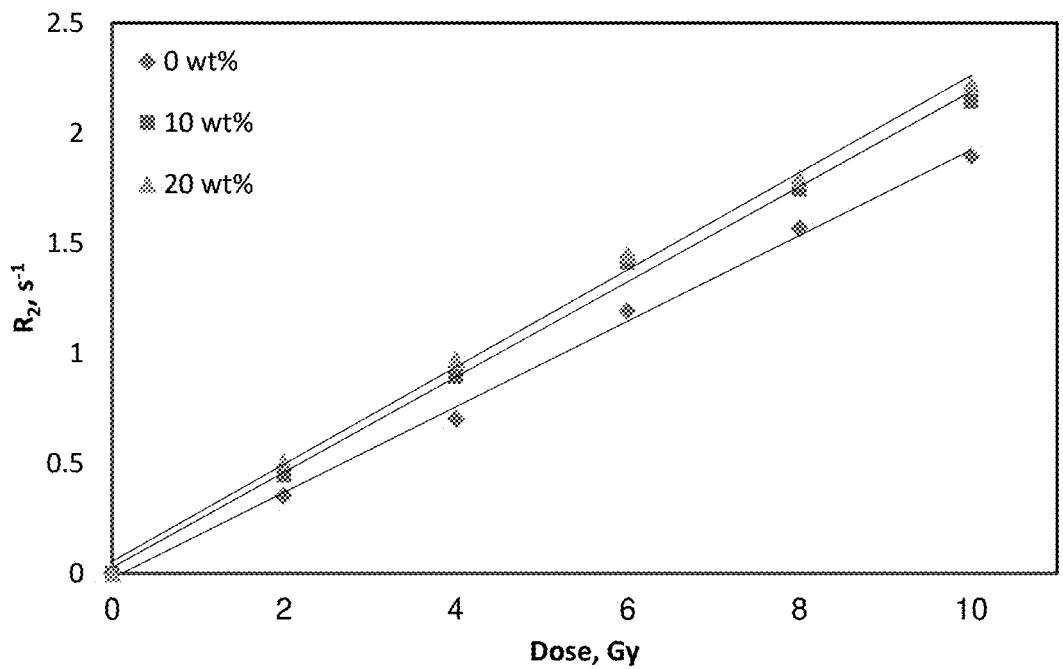
FIG. 3: Change in relaxation rate ($\Delta R2$) of NHMAGAT (1, 2 and 3) polymer gel with the different concentration of ethylene glycol.

FIG. 3 shows change in relaxation rate (ΔR2) of NHMAGAT (1, 2 and 3) polymer gel with the different concentration of ethylene glycol.

Figure 4:
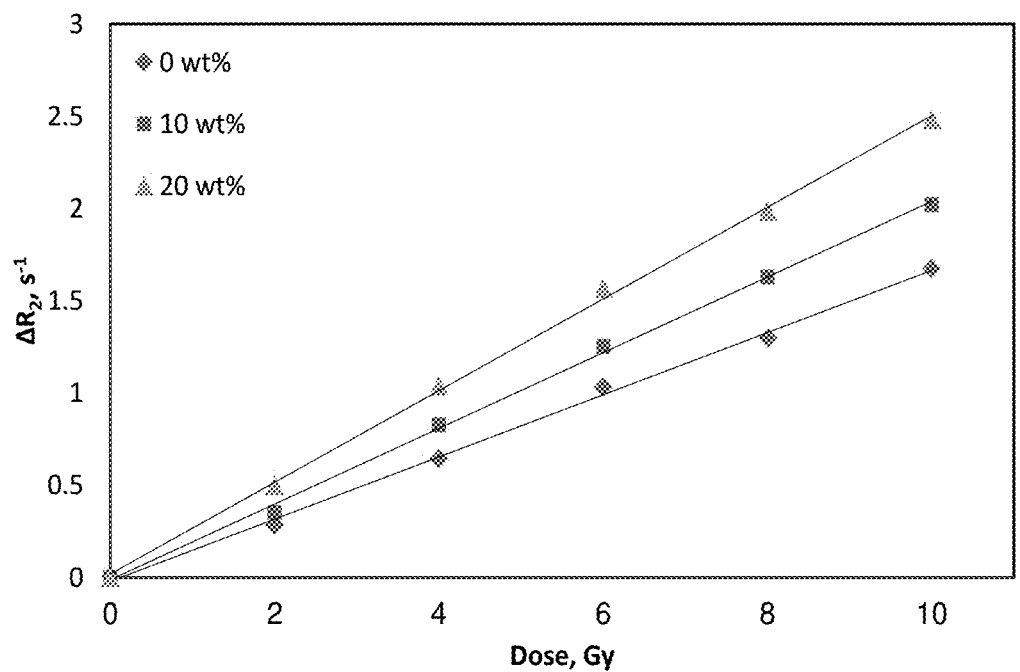
FIG. 4: Change in relaxation rate ($\Delta R2$) of DAAGAT (1, 2 and 3) polymer gel with the different concentration of ethylene glycol.

FIG. 4 shows change in relaxation rate (ΔR2) of DAAMGAT (1, 2 and 3) polymer gel with the different concentration of ethylene glycol.

Figure 5:
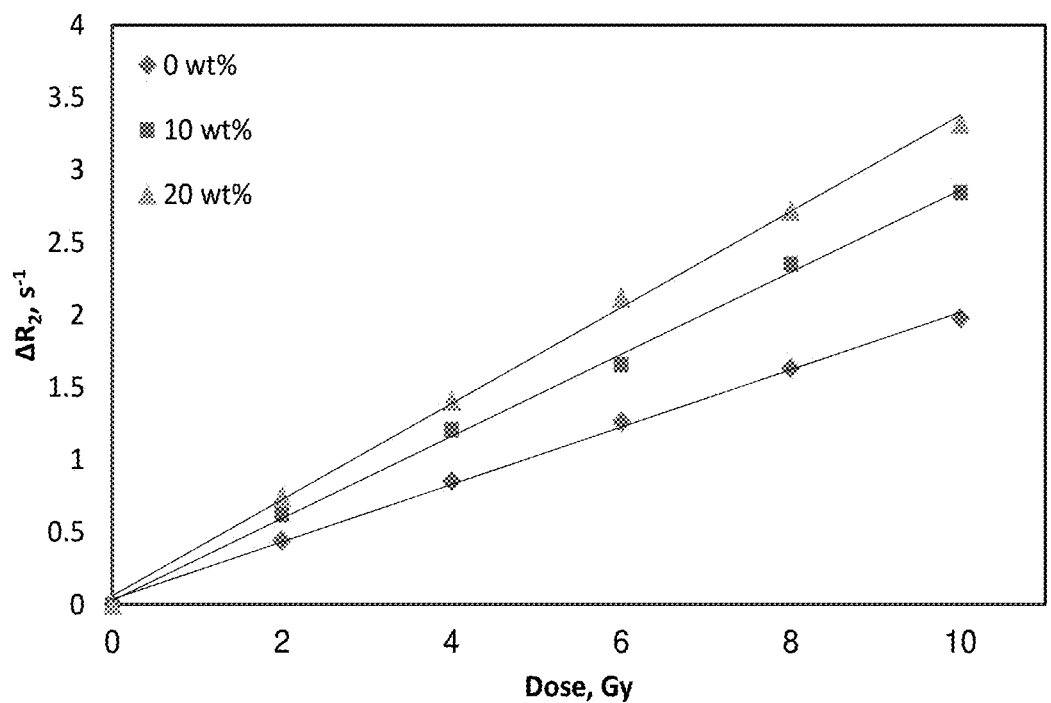
FIG. 5: Change in relaxation rate ($\Delta R2$) of NVCLGAT (1, 2 and 3) polymer gel with the different concentration of ethylene glycol.

FIG. 5 shows change in relaxation rate (ΔR2) of NVCLGAT (1, 2 and 3) polymer gel with the different concentration of ethylene glycol.

The performance of gel dosimeters in terms of dose sensitivity of these gels was calculated from the slope of linear plot of dose versus $\Delta R_2$ of FIGS. 1, 2, 3, 4 and 5. It was found in this invention the dose sensitivity value increases significantly with increase ethylene glycol concentration from 0 to 20 wt %, leading to the increase of polymerization of gel dosimeters as listed in table 5.

The effect of dose rate on the dose response of polymer gel dosimeters (PAGAT, NIMPAGAT, NHMAGAT, DAAMGAT and NVCLGAT) was conducted in this invention using 50 and 500 cGy/min with 6 MV radiation energy. The dosimeters were irradiated for absorbed doses of (2, 4, 6, 8 and 10) Gy. Three gel samples were irradiated for each dose point, and average $\Delta R_2$ values were obtained at the selected absorbed dose. The results show that the variation in dose response due to changing the dose rate for the five types of gels was less than 5% indicates the dose map can be acquired at any dose rate.

The dependence of the five gels response on radiation energy was also investigated. A set of three samples of (PAGAT, NIMPAGAT, NHMAGAT, DAAMGAT and NVCLGAT) was used for each dose and the average value was reported. Exposures were made using 6 and 15 MV at 200 Gy/min dose rate with absorbed doses from 2 to 10 Gy. Results show that there is no significant effect of radiation dose on the performance of these gel dosimeters (less than 4%).

The stability of unirradiated and irradiated polymer gel dosimeters was evaluated for the five types of gel dosimeters. For reliability and statistical study, a set of three samples was used for each selected dose. The samples were stored in a refrigerator (10° C.). It was found that there is no apparent change (less than 3%) in $\Delta R_2$ of the gel dosimeters up to one week.

What is claimed is:

1. A three-dimensional dosimeter gel, comprising;
   a) a N, N'-methylene-bis-acrylamide (BIS) cross-linker wt % from 1 to 4%;
   b) a Gelatin Type B wt % from 1 to 10%;
   c) a Tetrakis (hydroxymethyl) phosphonium chloride (THPC) from 5-20 mM;
   d) an Ethylene glycol wt % from 1 to 50%;
   e) a De-ionized water as a solvent; and
   f) a monomer in a specific range.

2. The three-dimensional dosimeter gel of claim 1, wherein the monomer is an Acrylamide (AAm) monomer and in the specific range from 1 to 10% wt %.

3. The three-dimensional dosimeter gel of claim 1, wherein the monomer is a N-Isopropylacrylamide (NIPAM) monomer and in the specific range from 2 to 4% wt %.

4. The three-dimensional dosimeter gel of claim 1, wherein the monomer is a N-(Hydroxymethyl) acrylamide (NHMA) monomer and in the specific range from 2 to 10% wt %.

5. The three-dimensional dosimeter gel of claim 1, wherein the monomer is a Diacetone acrylamide (DAAM) monomer and in the specific range from 2 to 10% wt %.

6. The three-dimensional dosimeter gel of claim 1, wherein the monomer is a N-Vinylcaprolactam (NVCL) monomer and in the specific range from 2 to 10% wt %.

7. A process of making a three-dimensional dosimeter gel, comprising;
   fabricating the three-dimensional dosimeter gel under a fume hood in normal atmospheric conditions.;

adding a gelatin Type B an ultra-pure de-ionized water and left for 10 minutes to soak before heating up to 50° C. for 1 hour;

cooling down to 45° C., and adding BIS, monomer and ethylene glycol respectively and kept stirring until completely dissolved;

after the solution cooled down to 35° C., THPC was added as antioxidant; the final polymer gels were filled into NMR tubes and sealed; and all gels were stored in a refrigerator (10° C.) overnight prior to irradiation.

8. The process of making the three-dimensional dosimeter gel of claim 7, wherein the monomer is an Acrylamide (AAm) monomer.

9. The process of making the three-dimensional dosimeter gel of claim 7, wherein the monomer is a N-Isopropylacrylamide (NIPAM) monomer.

10. The process of making the three-dimensional dosimeter gel of claim 7, wherein the monomer is a N-(Hydroxymethyl) acrylamide (NHMA) monomer and in the specific range from 2 to 10%.

11. The process of making the three-dimensional dosimeter gel of claim 7, wherein the monomer is a Diacetone acrylamide (DAAM) monomer and in the specific range from 2 to 10%.

12. The process of making the three-dimensional dosimeter gel of claim 7, wherein the monomer is a N-Vinylcaprolactam (NVCL) monomer and in the specific range from 2 to 10%.

13. A three-dimensional dosimeter gel, comprising;
a) a N, N'-methylene-bis-acrylamide (BIS) cross-linker wt % from 1 to 4%;
b) a Gelatin Type B wt % from 1 to 10%;
c) a Tetrakis (hydroxymethyl) phosphonium chloride (THPC) from 5-20 mM;
d) an Ethylene glycol wt % from 1 to 50%;
e) a De-ionized water as a solvent; and
f) a monomer in a specific range, wherein the monomer is a N-Vinylcaprolactam (NVCL) monomer and in the specific range from 2 to 10% wt %.

* * * * *